US007834022B2

(12) United States Patent
Rodgers et al.

(10) Patent No.: US 7,834,022 B2
(45) Date of Patent: Nov. 16, 2010

(54) METABOLITES OF THE JANUS KINASE INHIBITOR (R)-3-(4-(7H-PYRROLO[2,3-D] PYRIMIDIN-4-YL)-1H-PYRAZOL-1-YL)-3-CYCLOPENTYLPROPANENITRILE

(75) Inventors: James D. Rodgers, Landenberg, PA (US); Argyrios G. Arvantis, Kennett Square, PA (US); Jack Guoen Shi, Wilmington, DE (US); Stacey Shepard, Wilmington, DE (US)

(73) Assignee: Incyte Corporation, Wilmington, DE (US)

( * ) Notice: Subject to any disclaimer, the term of this patent is extended or adjusted under 35 U.S.C. 154(b) by 0 days.

(21) Appl. No.: 12/137,883

(22) Filed: Jun. 12, 2008

(65) Prior Publication Data

US 2008/0312258 A1    Dec. 18, 2008

Related U.S. Application Data

(60) Provisional application No. 60/943,695, filed on Jun. 13, 2007.

(51) Int. Cl.
| | | |
|---|---|---|
| C07D 487/04 | (2006.01) | |
| A61K 31/519 | (2006.01) | |
| A61P 37/06 | (2006.01) | |
| A61P 35/00 | (2006.01) | |
| A61P 25/28 | (2006.01) | |

(52) U.S. Cl. .................................. 514/265.1; 544/265
(58) Field of Classification Search ................. 544/280; 514/265.1
See application file for complete search history.

(56) References Cited

U.S. PATENT DOCUMENTS

| | | | |
|---|---|---|---|
| 5,521,184 | A | 5/1996 | Zimmermann |
| 6,335,342 | B1 | 1/2002 | Longo et al. |
| 6,486,322 | B1 | 11/2002 | Longo et al. |
| 6,579,882 | B2 | 6/2003 | Stewart et al. |
| 7,005,436 | B2 | 2/2006 | Lloyd et al. |
| 2003/0165576 | A1 | 9/2003 | Fujii et al. |
| 2004/0009983 | A1 | 1/2004 | Cox et al. |
| 2004/0198737 | A1 | 10/2004 | Cox et al. |
| 2005/0153989 | A1 | 7/2005 | Grotzfeld et al. |
| 2006/0106020 | A1 | 5/2006 | Rodgers et al. |
| 2006/0183761 | A1 | 8/2006 | Ledeboer et al. |
| 2006/0183906 | A1 | 8/2006 | Rodgers et al. |
| 2007/0135461 | A1* | 6/2007 | Rodgers et al. .......... 514/265.1 |
| 2007/0149506 | A1 | 6/2007 | Arvanitis et al. |
| 2008/0188500 | A1 | 8/2008 | Arvanitis et al. |

FOREIGN PATENT DOCUMENTS

| | | |
|---|---|---|
| DE | 30 36 390 | 5/1982 |
| WO | WO 97/02262 | 1/1997 |
| WO | WO 97/02266 | 1/1997 |
| WO | WO 99/62908 | 12/1999 |
| WO | WO 99/65908 | 12/1999 |
| WO | WO 99/65909 | 12/1999 |
| WO | WO 00/09495 | 2/2000 |
| WO | WO 00/53595 | 9/2000 |
| WO | WO 01/14402 | 3/2001 |
| WO | WO 01/42246 | 6/2001 |
| WO | WO 01/64655 | 9/2001 |
| WO | WO 02/00196 | 1/2002 |
| WO | WO 02/00661 | 1/2002 |
| WO | WO 02/055084 | 7/2002 |
| WO | WO 02/060492 | 8/2002 |
| WO | WO 02/096909 | 12/2002 |
| WO | WO 03/011285 | 2/2003 |
| WO | WO 03/024967 | 3/2003 |
| WO | WO 03/037347 | 5/2003 |
| WO | WO 03/048162 | 6/2003 |
| WO | WO 03/099771 | 12/2003 |
| WO | WO 2004/005281 | 1/2004 |
| WO | WO 2004/041814 | 5/2004 |
| WO | WO 2004/046120 | 6/2004 |
| WO | WO 2004/047843 | 6/2004 |
| WO | WO 2004/056786 | 7/2004 |
| WO | WO 2004/072063 | 8/2004 |
| WO | WO 2004/080980 | 9/2004 |
| WO | WO 2004/099204 | 11/2004 |
| WO | WO 2004/099205 | 11/2004 |
| WO | WO 2005/013986 | 2/2005 |
| WO | WO 2005/028444 | 3/2005 |
| WO | WO 2005/051393 | 6/2005 |
| WO | WO 2005/060972 | 7/2005 |
| WO | WO 2005/095400 | 10/2005 |

(Continued)

OTHER PUBLICATIONS

Adv Pharmacol. 2000;47:113-74.
Agents Actions. Jan. 1993;38(1-2):116-21.
26th Annual JPMorgan Healthcare Conference presentation dated Jan. 8, 2008.
Bell, Malcolm, and Zalay, Andrew, "Synthesis of Substituted 3-Amino[6, 5-b] triazinoindoles." Journal of Heterocyclic Chemistry, 12(5):1001-1004, Oct. 1975.
Bioreversible Carriers in Drug Design, ed. Edward B. Roche, American Pharmaceutical Association and Pergamon Press, 1987.
Blume-Jensen P et al, Nature 2001, 411(6835):355-365.
Bolen JB. Nonreceptor tyrosine protein kinases. Oncogene. 1993, 8(8):2025-31.
Borie, D.C. et al., Transplantation. Dec. 27, 2005;80(12):1756-64.
Boudny, V., and Kovarik, J., Neoplasm. 49:349-355, 2002.
Bowman, T., et al. Oncogene 19:2474-2488, 2000.

(Continued)

Primary Examiner—James O Wilson
Assistant Examiner—Susanna Moore
(74) Attorney, Agent, or Firm—Lahive & Cockfield, LLP; Brian C. Trinque; Pankaj N. Desai

(57) ABSTRACT

The present invention provides active metabolites of 3-(4-(7H-pyrrolo[2,3-d]pyrimidin-4-yl)-1H-pyrazol-1-yl)-3-cyclopentylpropanenitrile that modulate the activity of Janus kinases and are useful in the treatment of diseases related to activity of Janus kinases including, for example, immune-related diseases, skin disorders, myeloid proliferative disorders, cancer, and other diseases.

11 Claims, No Drawings

FOREIGN PATENT DOCUMENTS

| | | |
|---|---|---|
| WO | WO 2005/105146 | 11/2005 |
| WO | WO 2005/105814 | 11/2005 |
| WO | WO 2005/105988 | 11/2005 |
| WO | WO 2005/110410 | 11/2005 |
| WO | WO 2005/121130 | 12/2005 |
| WO | WO 2006/013114 | 2/2006 |
| WO | WO 2006/046023 | 5/2006 |
| WO | WO 2006/046024 | 5/2006 |
| WO | WO 2006/056399 | 6/2006 |
| WO | WO 2006/096270 | 9/2006 |
| WO | WO 2006/127587 | 11/2006 |
| WO | WO 2007/025090 | 3/2007 |
| WO | WO 2007/041130 | 4/2007 |
| WO | WO 2007/076423 | 7/2007 |
| WO | WO 2007/084557 | 7/2007 |
| WO | WO 2007/117494 | 10/2007 |

OTHER PUBLICATIONS

Burger, R., et al. Hematol J. 2:42-53, 2001.
Candotti, F., L. Notarangelo, et al. (2002). "Molecular aspects of primary immunodeficiencies: lessons from cytokine and other signaling pathways." J Clin Invest 109(10): 1261-9.
Candotti, F., S. A. Oakes, et al. (1997). "Structural and functional basis for JAK3-deficient severe combined immunodeficiency." Blood 90(10): 3996-4003.
Cetkovic-Cvrlje, M., A. L. Dragt, et al. (2003). "Targeting JAK3 with JANEX-1 for prevention of autoimmune type 1 diabetes in NOD mice." Clin Immunol 106(3): 213-25.
Chalandon, Yves, and Schwaller, Jürg, "Targeting mutated protein tyrosine kinases and their signaling pathways in hematologic malignancies." Hematologica, 90:949-968, 2005.
Changelian, P.S. et al. Science, 2003, 302, 875-878.
Chen, C.L. et al., "Stat3 Activation in Human Endometrial and Cervical Cancer", British journal of Cancer, 96,, 591-599, 2007.
Conklyn, M. et al., Journal of Leukocyte Biology, 2004, 76, 1248-1255.
Daniels et al., "Imatinib mesylate inhibits the profibrogenic activity of TGF-β and prevents bleomycinmediated lung fibrosis," J. Clin. Invest., 114(9):1308-1316, Nov. 2004.
Deuse, T. et al., Transplantation, 2008, 85(6) 885-892.
Doleschall G., and Lempert, K. "Thermal and Acid Catalysed Degradations of 3-Alkylthio-6,7-Dihydro-[1.2.4]Triazino[1.6-c]Quinazolin-5-Ium-1-Olates." Tetrahedron, 30:3997-4012, 1974.
De Vos, J., M. Jourdan, et al. (2000). "JAK2 tyrosine kinase inhibitor tyrphostin AG490 downregulates the mitogen-activated protein kinase (MAPK) and signal transducer and activator of transcription (STAT) pathways and induces apoptosis in myeloma cells." Br J Haematol 109(4): 823-8.
Dudley, A.C. et al. Biochem. J. 2005, 390(Pt 2):427-36.
E. Quesada et al, Tetrahedron, 62 (2006) 6673-6680.
Fridman, Jordan, et al. "Discovery and Preclinical Development of Selective JAK Inhibitors for the Treatment of Hematological Malignancies" poster presented at European Hematology Association, 12th Congress, Vienna, Austria. Abstract 0324, Jun. 8, 2007.
Fridman, Jordan, et al. "Discovery and Preclinical Development of Selective JAK Inhibitors for the Treatment of Myeloproliferative Disorders" poster presented at the 4th International Congress on Myeloproliferative Diseases and Myelodysplastic Syndromes, New York, NY. Nov. 8-10, 2007. Poster 0009.
Fridman, Jordan et al. "Efficacy and Tolerability of Novel JAK Inhibitors in Animal Models of Rheumatoid Arthritis" poster presented at the ACR/ARHP (American College of Rheumatology/Association of Rheumatology Health Professionals) Scientific Meeting 2007, Boston, MA. Nov. 10, 2007. Abstract 1771, poster 285.
Fridman, Jordan et al. "Discovery and Preclinical Characterization of INCB018424, a Selective JAK2 Inhibitor for the Treatment of Myeloproliferative Disorders" poster presented at the American Society of Hematology, 49th Annual Meeting and Exposition, GA. Abstract #3538, poster #757, Dec. 10, 2007.
Fridman, J. et al. "Selective JAK Inhibition is Efficacious against Multiple Myeloma Cells and Reverses the Protective Effects of Cytokine and Stromal Cell Support" Abstract #0956, presented Sunday, Jun. 15, 2008 at the European Hematology Association, 13$^{th}$ Congress, Jun. 12-15, Copenhagen, Denmark.
Gorre, M.E. et al., "Clinical Resistance to STI-571 Cancer Therapy Caused by BCR-ABL Gene Mutation or Amplification." Science, 293:876, 2001.
Gotlieb, Alice, Presentation at the 2008 American Academy of Dermatology, 66th Annual Meeting, San Antonio, TX. Feb, 1, 2008, symposium-303.
Gottlieb, A.B., et al, Nat Rev Drug Disc., 2008, 4:19-34.
"INCB18424 Discussion" presentation at the American Society of Hematology, 49th Annual Meeting and Exposition, Atlanta, GA. Abstract #558, Dec. 10, 2008.
Immunol Today. Jan. 1998;19(1):37-44.
Ishizaki, T. et al. Molecular Pharmacology, 2000, 57, 976-983.
Itagaki, Noriaki; Kimura, Mari; Sugahara, Tsutomu; Iwabuchi, Yoshiharu. (Organic Letters 2005; 7(19); 4181-4183.
James, C., et al. Nature 434:1144-1148, (2005).
Journal of Pharmaceutical Science, 66, 2 (1977).
Kawamura, M., D. W. McVicar, et al. (1994). "Molecular cloning of L-JAK, a Janus family protein-tyrosine kinase expressed in natural killer cells and activated leukocytes." Proc Natl Acad Sci U S A 91(14): 6374-8).
Kharas, Michael, and Fruman, David, "ABL Oncogenes and Phosphoinositide 3-Kinase: Mechanism of Activation and Downstream Effectors." Cancer Res., 65(6):2047-2053, Mar. 15, 2005.
Kruh et al., "The complete coding sequence of arg defines the Abelson subfamily of cytoplasmic tyrosine kinases." Proc. Natl. Acad. Sci., 87:5802-5806, Aug. 1990.
Kubinyi, H. "QSAR: Hansch Analysis and Related Approaches," Methods and Principles in Medicinal Chemistry, Manhold, R. ed. Weinhein, NY, 1993.
Kudelacz, E. et al. European Journal of Pharmacology 582 (2008) 154-161.
Levine, et al., Cancer Cell, vol. 7, 2005: 387-397.
Madhusudan S, Ganesan TS. Tyrosine kinase inhibitors in cancer therapy. Clin Biochem. 2004, 37(7):618-35.
Manning, G. et al., Science. 2002, 298(5600):1912-1934.
Methods in Molecular Biology: vol. 225, Inflammation Protocols., Winyard, P.G. and Willoughby, D.A., Humana Press, 2003.
Milici, A.J., et al., Arthritis Research & Therapy 2008, 10:R14 (http://arthritis-research.com/content/10/1/R14).
Nakagawara, Akira, "Trk receptor tyrosine kinases: A bridge between cancer and neural development." Cancer Letters, 169:107-114, 2001.
Neubauer, H., A. Cumano, et al. (1998). Cell 93(3): 397-409.
Nishio, M. et al. FEBS Letters, 1999, 445, 87-91.
Palmer, Amparo, and Klein, Rudiger, "Multiple roles of ephrins in morphogenesis, neuronal networking, and brain function." *Genes & Dev.*, 17:1429-1450, 2003.
Patani, G.A. et al. Chem. Rev. 1996, 96, 3147-3176.
Parganas, E., D. Wang, et al. (1998). Cell 93(3): 385-95.
Park et al., Analytical Biochemistry 1999, 269, 94-104.
Pernis, A. B. and P. B. Rothman (2002). "JAK-STAT signaling in asthma." J Clin Invest 109(10): 1279-83.
Pirard, B. et al. J. Chem. Inf. Comput. Sci. 2000, 40, 1431-1440.
Press Release dated Sep. 18, 2008: "Incyte's Topical JAK Inhibitor Demonstrates Positive Proof-of-Concept Results in Patients with Mild to Moderate Psoriasis".
Poster/presentation by Punwani et al. "Initial Efficacy and Safety of Topical INCYB018424 Cream, a Selective Janus Kinase 1&2 (JAK 1&2) Inhibitor in Psoriasis" 17$^{th}$ Congress of the European Academy of Dermatology and Venereology, Paris, France, Sep. 17, 2008.
Remington's Pharmaceutical Sciences, 17th ed., Mack Publishing Company, Easton, Pa., 1985, p. 1418.
Rodig, S. J., M. A. Meraz, et al. (1998). "Disruption of the Jak1 gene demonstrates obligatory and nonredundant roles of the Jaks in cytokine-induced biologic responses." Cell 93(3): 373-83.
Rousvoal, G. et al. Transpl Int. Dec. 2006;19(12):1014-21.

Saemann, M. D., C. Diakos, et al. (2003). "Prevention of CD40-triggered dendritic cell maturation and induction of T-cell hyporeactivity by targeting of Janus kinase 3." Am J Transplant 3(11): 1341-9.

Scott, M. J., C. J. Godshall, et al. (2002). "Jaks, STATs, Cytokines, and Sepsis." Clin Diagn Lab Immunol 9(6): 1153-9.

Seto, Y., H. Nakajima, et al. (2003). "Enhanced Th2 cell-mediated allergic inflammation in Tyk2-deficient mice." J Immunol 170(2): 1077-83.

Shah et al., "Multiple BCR-ABL kinase domain mutations confer polyclonal resistance to the tyrosine kinase inhibitor imatinib (STI571) in chronic phase and blast crisis chronic myeloid leukemia." Cancer Cell, 2:117-125, Aug. 2002.

Sriram, K. et al. J. Biol. Chem. 2004, 279(19):19936-47. Epub Mar. 2, 2004.

Staerk, J., et al. JBC 280:41893-41899, (2005).

T. Higuchi and V. Stella, "Pro-drugs as Novel Delivery Systems," vol. 14 of the A.C.S. Symposium Series, 1975.

T.W. Green and P.G.M. Wuts, Protective Groups in Organic Synthesis, 3rd. Ed., Wiley & Sons, Inc., New York (1999).

Takemoto, S., J. C. Mulloy, et al. (1997). "Proliferation of adult T cell leukemia/lymphoma cells is associated with the constitutive activation of JAK/STAT proteins." Proc Natl Acad Sci U S A 94(25): 13897-902.

Thompson, J.E., et al. Bioorganic & Medicinal Chemistry Letters 12 (2002) 1219-1223.

Verstovsek, S. et al. INCB18424, an Oral, Selective JAK2 Inhibitor, Shows Significant Clinical Activity in a Phase I/II Study in Patient with Primary Myelofibrosis (PMF) and Post Polycythemia Vera/Essential Thrombocythemia Myelofibrosis (Post-PV/ET MF), presentation at the American Society of Hematology 49th Annual Meeting and Exposition, Dec. 10, 2007.

Verstovsek, S. et al. "The selective Janus kinase (JAK) inhibitor, INCB018424, shows efficacy in phase I/II trial in patients with primary myelofibrosis (PMF) and post polycythemia vera/essential thrombocythemia myelofibrosis (Post-PV/ET MF)" Abstract #0444, presented Saturday, Jun. 14, 2008 at the European Hematology Association, 13th Congress, Jun. 12-15, Copenhagen, Denmark.

Wu T.Y.H., et al. Organic Letters, 2003, 5(20), 3587-3590.

Zou, Xiaoming, and Calame, Kathryn, "Signaling Pathways Activated by Oncogenic Forms of Abl Tyrosine Kinase." Journal of Biological Chemistry, 274(26):18141-18144, 1999.

International Search Report and Written Opinion for PCT/US2006/047369, 16 pages, (Apr. 24, 2007).

Abstract of Chilean patent application No. 3496-06, published in Official Gazette of the Republic of Chile (Jun. 1, 2007) (1 page + 1 page translation).

Letter from Chilean foreign counsel reporting the publication of the abstract of Chilean patent application No. 3496-06 (Jun. 5, 2007) (1 page).

* cited by examiner

METABOLITES OF THE JANUS KINASE INHIBITOR (R)-3-(4-(7H-PYRROLO[2,3-D]PYRIMIDIN-4-YL)-1H-PYRAZOL-1-YL)-3-CYCLOPENTYLPROPANENITRILE

CROSS-REFERENCE TO RELATED APPLICATIONS

This application claims the benefit of U.S. Ser. No. 60/943,695, filed Jun. 13, 2007, the disclosure of which is incorporated herein by reference in its entirety.

FIELD OF THE INVENTION

The present invention provides active metabolites of (R)-3-(4-(7H-pyrrolo[2,3-d]pyrimidin-4-yl)-1H-pyrazol-1-yl)-3-cyclopentylpropanenitrile that modulate the activity of Janus kinases and are useful in the treatment of diseases related to activity of Janus kinases including, for example, immune-related diseases, skin disorders, myeloid proliferative disorders, cancer, and other diseases.

BACKGROUND OF THE INVENTION

Protein kinases (PKs) are a group of enzymes that regulate diverse, important biological processes including cell growth, survival and differentiation, organ formation and morphogenesis, neovascularization, tissue repair and regeneration, among others. Protein kinases exert their physiological functions through catalyzing the phosphorylation of proteins (or substrates) and thereby modulating the cellular activities of the substrates in various biological contexts. In addition to the functions in normal tissues/organs, many protein kinases also play more specialized roles in a host of human diseases including cancer. A subset of protein kinases (also referred to as oncogenic protein kinases), when dysregulated, can cause tumor formation and growth, and further contribute to tumor maintenance and progression (Blume-Jensen P et al, Nature 2001, 411(6835):355-365). Thus far, oncogenic protein kinases represent one of the largest and most attractive groups of protein targets for cancer intervention and drug development.

The Janus Kinase (JAK) family plays a role in the cytokine-dependent regulation of proliferation and function of cells involved in immune response. Currently, there are four known mammalian JAK family members: JAK1 (also known as Janus kinase-1), JAK2 (also known as Janus kinase-2), JAK3 (also known as Janus kinase, leukocyte; JAKL; L-JAK and Janus kinase-3) and TYK2 (also known as protein-tyrosine kinase 2). The JAK proteins range in size from 120 to 140 kDa and comprise seven conserved JAK homology (JH) domains; one of these is a functional catalytic kinase domain, and another is a pseudokinase domain potentially serving a regulatory function and/or serving as a docking site for STATs (Scott, Godshall et al. 2002, supra).

Blocking signal transduction at the level of the JAK kinases holds promise for developing treatments for human cancers. Inhibition of the JAK kinases is also envisioned to have therapeutic benefits in patients suffering from skin immune disorders such as psoriasis, and skin sensitization. Accordingly, inhibitors of Janus kinases or related kinases are widely sought and several publications report effective classes of compounds. For example, certain JAK inhibitors, including (R)-3-(4-(7H-pyrrolo[2,3-d]pyrimidin-4-yl)-1H-pyrazol-1-yl)-3-cyclopentylpropanenitrile shown below, are reported in U.S. Ser. No. 11/637,545, filed Dec. 12, 2006.

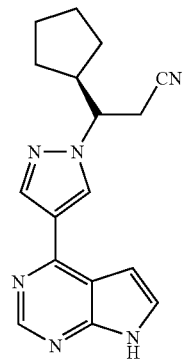

Thus, new or improved agents which inhibit kinases such as Janus kinases are continually needed for developing new and more effective pharmaceuticals to treat cancer and other diseases. The metabolites, compositions and methods described herein are directed toward these needs and other ends.

SUMMARY OF THE INVENTION

The present invention provides a compound selected from:

3-(4-(7H-pyrrolo[2,3-d]pyrimidin-4-yl)-1H-pyrazol-1-yl)-3-(3-hydroxycyclopentyl)propanenitrile;

3-(4-(7H-pyrrolo[2,3-d]pyrimidin-4-yl)-1H-pyrazol-1-yl)-3-(2-hydroxycyclopentyl)propanenitrile; and 3-(4-(7H-pyrrolo[2,3-d]pyrimidin-4-yl)-1H-pyrazol-1-yl)-3-(3-oxocyclopentyl)propanenitrile;

or pharmaceutically acceptable salt thereof.

The present invention further provides one or more of the above compounds, or pharmaceutically acceptable salts thereof, in substantially isolated form.

The present invention further provides compositions comprising a compound of the invention, or pharmaceutically acceptable salt thereof, and at least one pharmaceutically acceptable carrier.

The present invention further provides methods of modulating an activity of JAK comprising contacting JAK with a compound of the present invention, or pharmaceutically acceptable salt thereof.

The present invention further provides methods of treating a disease in a patient, comprising administering to the patient a therapeutically effective amount of a compound of the invention, or pharmaceutically acceptable salt thereof.

DETAILED DESCRIPTION

The present invention provides, inter alia, compounds that are active metabolites of the JAK inhibitor (R)-3-(4-(7H-pyrrolo[2,3-d]pyrimidin-4-yl)-1H-pyrazol-1-yl)-3-cyclopentylpropanenitrile. These metabolites modulate the activity of one or more JAKs and are useful, for example, in the treatment of diseases associated with JAK expression or activity. The metabolites of the invention are indicated in Table 1 below. Structures are intended to encompass all possible stereoisomers.

TALBE 1

| Reference | Name | Structure |
|---|---|---|
| Metabolite 1 | 3-(4-(7H-pyrrolo[2,3-d]pyrimidin-4-yl)-1H-pyrazol-1-yl)-3-(3-hydroxycyclopentyl)propanenitrile | 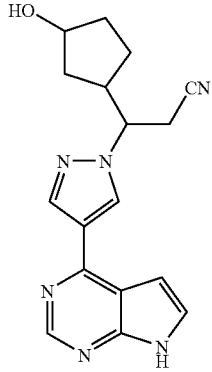 |
| Metabolite 2 | 3-(4-(7H-pyrrolo[2,3-d]pyrimidin-4-yl)-1H-pyrazol-1-yl)-3-(2-hydroxycyclopentyl)propanenitrile | 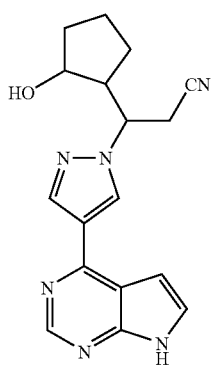 |
| Metabolite 3 | 3-(4-(7H-pyrrolo[2,3-d]pyrimidin-4-yl)-1H-pyrazol-1-yl)-3-(3-oxocyclopentyl)propanenitrile | 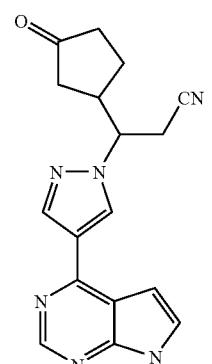 |

The metabolites of the invention were isolated from rat or dog urine samples collected from pharmacokinetic and toxicokinetic studies of the JAK inhibitor (R)-3-(4-(7H-pyrrolo[2,3-d]pyrimidin-4-yl)-1H-pyrazol-1-yl)-3-cyclopentylpropanenitrile (Compound 1). As shown in Table 2 and detailed in Example A, the metabolites are active and potent JAK inhibitors, and have advantageous properties related to significantly higher free fractions and higher metabolic stability in human microsomes compared with Compound 1. This data suggests the present metabolites may desirably have a longer elimination half-life in humans than does Compound 1.

In some embodiments, the metabolites of the invention are substantially isolated. By "substantially isolated" is meant that the compound is at least partially or substantially separated from the environment in which it was formed or detected. Partial separation can include, for example, a composition enriched in the compound of the invention. Substantial separation can include compositions containing at least about 50%, at least about 60%, at least about 70%, at least about 80%, at least about 90%, at least about 95%, at least about 97%, or at least about 99% by weight of the metabolite.

The present invention also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the conventional non-toxic salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., 1985, p. 1418 and *Journal of Pharmaceutical Science*, 66, 2 (1977), each of which is incorporated herein by reference in its entirety.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The metabolites are asymmetric (e.g., having one or more stereocenters). All stereoisomers, such as enantiomers and diastereomers, are intended unless otherwise indicated. Methods on how to prepare optically active forms from optically active starting materials are known in the art, such as by resolution of racemic mixtures or by stereoselective synthesis.

Compounds of the invention also include all isotopes of atoms occurring in the metabolites. Isotopes include those atoms having the same atomic number but different mass numbers. For example, isotopes of hydrogen include tritium and deuterium.

The term, "compound," as used herein is meant to include all stereoisomers, geometric isomers, tautomers, and isotopes of the structures depicted.

Synthesis

Compounds of the invention, including salts thereof, can be prepared using known organic synthesis techniques and can be synthesized according to any of numerous possible synthetic routes.

The reactions for preparing compounds of the invention can be carried out in suitable solvents which can be readily selected by one of skill in the art of organic synthesis. Suitable solvents can be substantially nonreactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of compounds of the invention can involve the protection and deprotection of various chemical groups. The need for protection and deprotection, and the selection of appropriate protecting groups, can be readily determined by one skilled in the art. The chemistry of protecting groups can be found, for example, in T. W. Greene and P. G. M. Wuts, *Protective Groups in Organic Synthesis*, 3rd. Ed., Wiley & Sons, Inc., New York (1999), which is incorporated herein by reference in its entirety.

Reactions can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), or mass spectrometry, or by chromatography such as high performance liquid chromatography (HPLC) or thin layer chromatography.

Compounds of the invention can be prepared according to numerous preparatory routes known in the literature. Example synthetic methods for preparing compounds of the invention are provided in the Schemes below.

As shown in Scheme 1, synthesis of the diastereomeric mixture of the cis alcohols I starts with cyclopentene carboxylic acid 1. Cyclopentene carboxylic acid 1 is bromolactonized following a procedure described earlier (Hodgson, David M.; Witherington, Jason; Moloney, Brian A., *Journal of the Chemical Society, Perkin Transactions* 1: *Organic and Bio-Organic Chemistry*, 1994, 23, 3950) to give the corresponding bromolactone 2. The bromolactone 2 is debrominated with the use of a dehalogenating agent, such as (Me$_3$Si)$_3$SiH to give 3. The lactone 3 is reduced to the corresponding hemiketal with the use of a reducing agent, such as DIBAL-H; the hemiketal formed is treated directly with the ylid 3a to give the crotonitrile derivative 4. The nitrile 4 then reacts with the pyrazole 5 in the presence of a base such as DBU to give 6 as a mixture of diastereomers, which is converted to the alcohols I after removal of the SEM group. The individual stereoisomers of this mixture (I) can be separated by chiral chromatography to give the enantiomerically pure alcohols (4 total stereoisomers).

Scheme 1

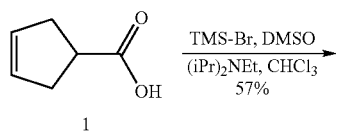

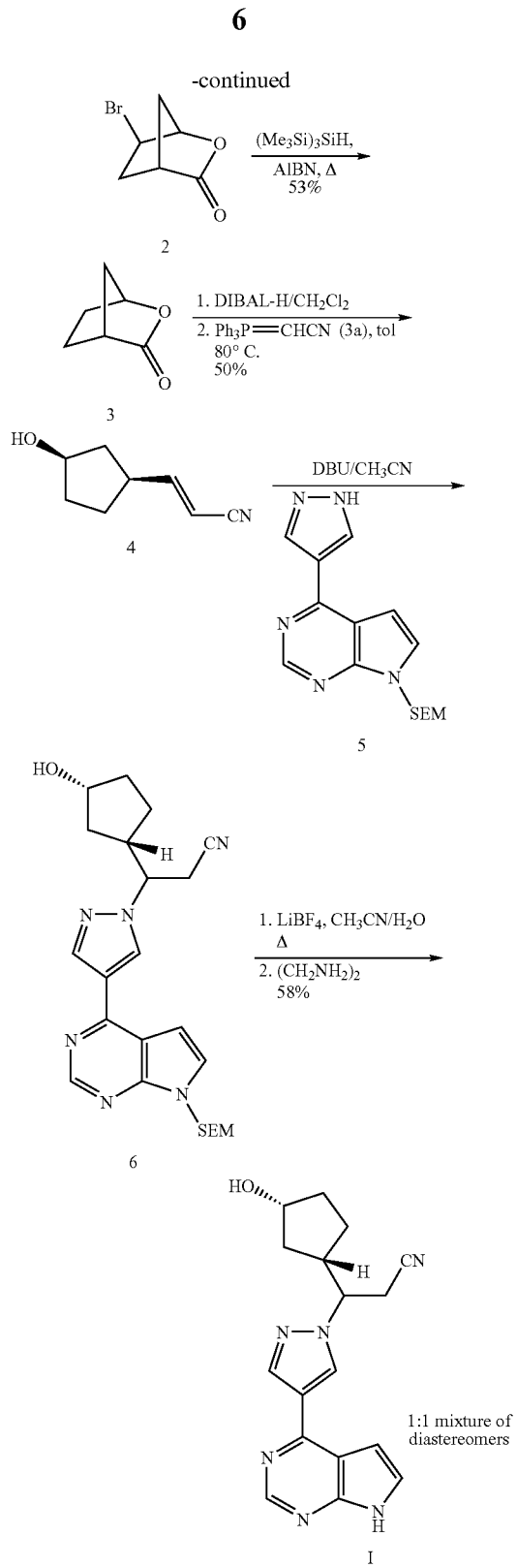

As shown in Scheme 2, the synthesis of the trans alcohols II starts with the diastereomeric mixture of alcohols 6. The diastereomeric mixture of alcohols 6 is treated with benzoic acid under the Mitsunobu conditions to give a mixture of the trans benzoates 7 with complete inversion. The mixture of the benzoates 7 is hydrolyzed by treatment with a base such as LiOH to give a mixture of the trans alcohols 8. The SEM group within the alcohols 8 is then removed to give the diastereomeric mixture of the trans alcohols II, which is separated by chiral chromatography to give individual stereoisomers (4 total stereoisomers).

Scheme 2

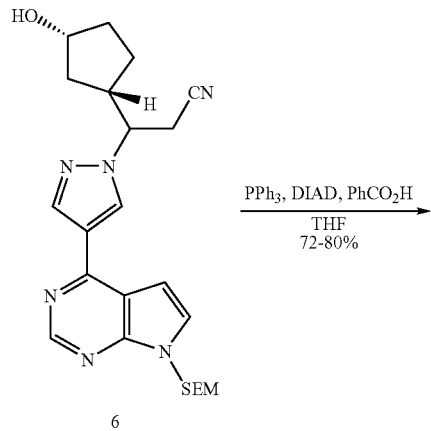

6

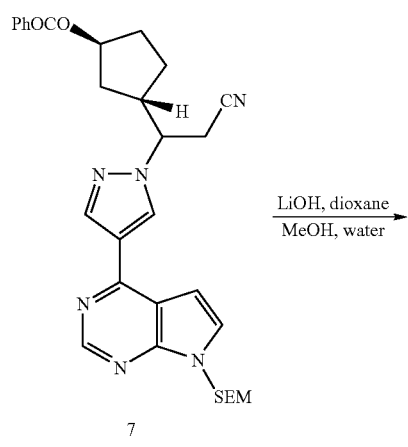

7

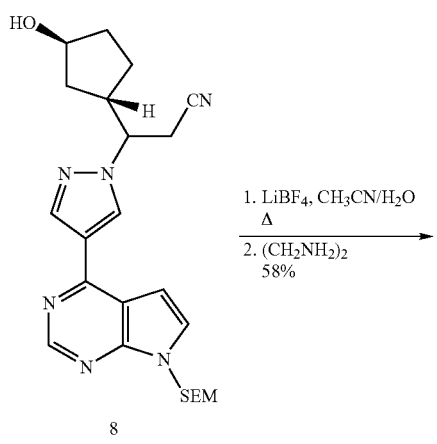

8

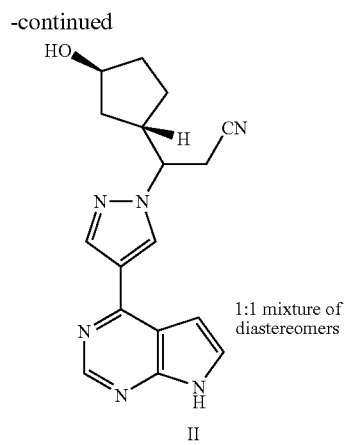

II

1:1 mixture of diastereomers

The synthesis of the ketones III is described in Scheme 3. A mixture of the cis alcohols 6 can be oxidized under Swern conditions to give the corresponding mixture of ketones 9. The SEM group within the ketones 9 is removed to give a mixture of the ketone III, which can be separated by chiral chromatography to give the individual stereoisomers (4 total stereoisomers).

Scheme 3

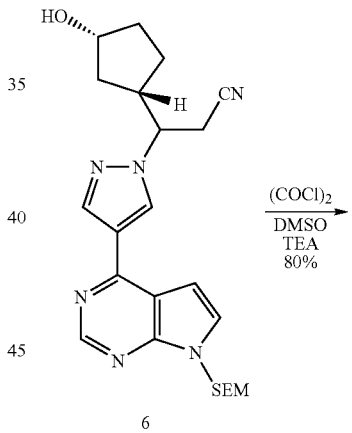

6

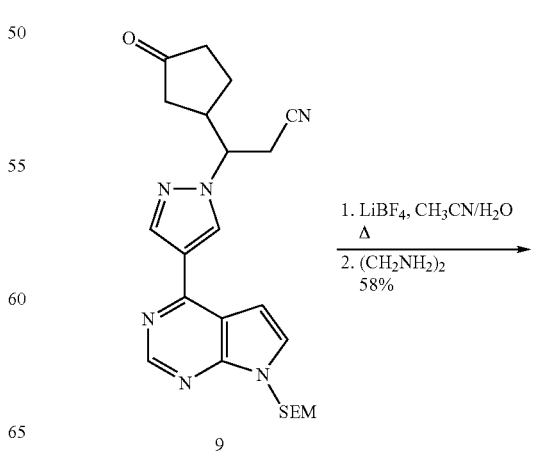

9

-continued

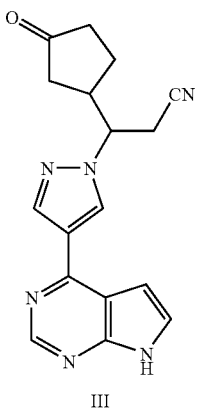

III

Methods

Compounds of the invention can modulate activity of one or more Janus kinases (JAKs). The term "modulate" is meant to refer to an ability to increase or decrease the activity of one or more members of the JAK family of kinases. Accordingly, compounds of the invention can be used in methods of modulating a JAK by contacting the JAK with any one or more of the compounds or compositions described herein. In some embodiments, compounds of the present invention can act as inhibitors of one or more JAKs. In some embodiments, compounds of the present invention can act to stimulate the activity of one or more JAKs. In further embodiments, the compounds of the invention can be used to modulate activity of a JAK in an individual in need of modulation of the receptor by administering a modulating amount of a compound of the invention.

JAKs to which the present compounds bind and/or modulate include any member of the JAK family. In some embodiments, the JAK is JAK1, JAK2, JAK3 or TYK2. In some embodiments, the JAK is JAK1 or JAK2. In some embodiments, the JAK is JAK2. In some embodiments, the JAK is JAK3.

The compounds of the invention can be selective. By "selective" is meant that the compound binds to or inhibits a JAK with greater affinity or potency, respectively, compared to at least one other JAK. In some embodiments, the compounds of the invention are selective inhibitors of JAK1 or JAK2 over JAK3 and/or TYK2. In some embodiments, the compounds of the invention are selective inhibitors of JAK2 (e.g., over JAK1, JAK3 and TYK2). Without wishing to be bound by theory, because inhibitors of JAK3 can lead to immunosuppressive effects, a compound which is selective for JAK2 over JAK3 and which is useful in the treatment of cancer (such as multiple myeloma, for example) can offer the additional advantage of having fewer immunosuppressive side effects. Selectivity can be at least about 5-fold, 10-fold, at least about 20-fold, at least about 50-fold, at least about 100-fold, at least about 200-fold, at least about 500-fold or at least about 1000-fold. Selectivity can be measured by methods routine in the art. In some embodiments, selectivity can be tested at the Km of each enzyme. In some embodiments, selectivity of compounds of the invention for JAK2 over JAK3 can be determined by the cellular ATP concentration.

Another aspect of the present invention pertains to methods of treating a JAK-associated disease or disorder in an individual (e.g., patient) by administering to the individual in need of such treatment a therapeutically effective amount or dose of a compound of the present invention or a pharmaceutical composition thereof A JAK-associated disease can include any disease, disorder or condition that is directly or indirectly linked to expression or activity of the JAK, including overexpression and/or abnormal activity levels. A JAK-associated disease can also include any disease, disorder or condition that can be prevented, ameliorated, or cured by modulating JAK activity.

Examples of JAK-associated diseases include diseases involving the immune system including, for example, organ transplant rejection (e.g. allograft rejection and graft versus host disease).

Further examples of JAK-associated diseases include autoimmune diseases such as multiple sclerosis, rheumatoid arthritis, juvenile arthritis, type I diabetes, lupus, psoriasis, inflammatory bowel disease, ulcerative colitis, Crohn's disease, myasthenia gravis, immunoglobulin nephropathies, autoimmune thyroid disorders, and the like. In some embodiments, the autoimmune disease is an autoimmune bullous skin disorder such as pemphigus vulgaris (PV) or bullous pemphigoid (BP).

Further examples of JAK-associated diseases include allergic conditions such as asthma, food allergies, atopic dermatitis and rhinitis. Further examples of JAK-associated diseases include viral diseases such as Epstein Barr Virus (EBV), Hepatitis B, Hepatitis C, HIV, HTLV 1, Varicella-Zoster Virus (VZV) and Human Papilloma Virus (HPV).

Further examples of JAK-associated diseases or conditions include skin disorders such as psoriasis (for example, psoriasis vulgaris), atopic dermatitis, skin rash, skin irritation, skin sensitization (e.g., contact dermatitis or allergic contact dermatitis). For example, certain substances including some pharmaceuticals when topically applied can cause skin sensitization. In some embodiments, co-administration or sequential administration of at least one JAK inhibitor of the invention together with the agent causing unwanted sensitization can be helpful in treating such unwanted sensitization or dermatitis. In some embodiments, the skin disorder is treated by topical administration of at least one JAK inhibitor of the invention.

In further embodiments, the JAK-associated disease is cancer including those characterized by solid tumors (e.g., prostate cancer, renal cancer, hepatic cancer, pancreatic cancer, gastric cancer, breast cancer, lung cancer, cancers of the head and neck, thyroid cancer, glioblastoma, Kaposi's sarcoma, Castleman's disease, melanoma etc.), hematological cancers (e.g., lymphoma, leukemia such as acute lymphoblastic leukemia, acute myelogenous leukemia (AML) or multiple myeloma), and skin cancer such as cutaneous T-cell lymphoma (CTCL) and cutaneous B-cell lymphoma. Example cutaneous T-cell lymphomas include Sezary syndrome and mycosis fungoides.

JAK-associated diseases can further include those characterized by expression of a mutant JAK2 such as those having at least one mutation in the pseudo-kinase domain (e.g. JAK2V617F).

JAK-associated diseases can further include myeloproliferative disorders (MPDs) such as polycythemia vera (PV), essential thrombocythemia (ET), myeloid metaplasia with myelofibrosis (MMM), chronic myelogenous leukemia (CML), chronic myelomonocytic leukemia (CMML), hypereosinophilic syndrome (HES), systemic mast cell disease (SMCD), and the like.

Further JAK-associated diseases include inflammation and inflammatory diseases. Example inflammatory diseases include inflammatory diseases of the eye (e.g., iritis, uveitis, scleritis, conjunctivitis, or related disease), inflammatory diseases of the respiratory tract (e.g., the upper respiratory tract including the nose and sinuses such as rhinitis or sinusitis or the lower respiratory tract including bronchitis, chronic obstructive pulmonary disease, and the like), inflammatory myopathy such as myocarditis, and other inflammatory diseases. Other inflammatory diseases treatable by the compounds of the invention include systemic inflammatory response syndrome (SIRS) and septic shock.

The JAK inhibitors described herein can further be used to treat ischemia reperfusion injuries or a disease or condition related to an inflammatory ischemic event such as stroke or cardiac arrest. The JAK inhibitors described herein can further be used to treat anorexia, cachexia, or fatigue such as that resulting from or associated with cancer. The JAK inhibitors described herein can further be used to treat restenosis, sclerodermitis, or fibrosis. The JAK inhibitors described herein can further be used to treat conditions associated with hypoxia or astrogliosis such as, for example, diabetic retinopathy, cancer, or neurodegeneration. See, e.g., Dudley, A. C. et al. *Biochem. J.* 2005, 390(Pt 2):427-36 and Sriram, K. et al. *J. Biol. Chem.* 2004, 279(19):19936-47. Epub Mar. 2, 2004.

The JAK inhibitors described herein can further be used to treat gout and increased prostate size due to, e.g., benign prostatic hypertrophy or benign prostatic hyperplasia.

As used herein, the term "contacting" refers to the bringing together of indicated moieties in an in vitro system or an in vivo system. For example, "contacting" a JAK with a compound of the invention includes the administration of a compound of the present invention to an individual or patient, such as a human, having a JAK, as well as, for example, introducing a compound of the invention into a sample containing a cellular or purified preparation containing the JAK.

As used herein, the term "individual" or "patient," used interchangeably, refers to any animal, including mammals, preferably mice, rats, other rodents, rabbits, dogs, cats, swine, cattle, sheep, horses, or primates, and most preferably humans.

As used herein, the phrase "therapeutically effective amount" refers to the amount of active compound or pharmaceutical agent that elicits the biological or medicinal response that is being sought in a tissue, system, animal, individual or human by a researcher, veterinarian, medical doctor or other clinician.

As used herein, the term "treating" or "treatment" refers to one or more of (1) preventing the disease; for example, preventing a disease, condition or disorder in an individual who may be predisposed to the disease, condition or disorder but does not yet experience or display the pathology or symptomatology of the disease; (2) inhibiting the disease; for example, inhibiting a disease, condition or disorder in an individual who is experiencing or displaying the pathology or symptomatology of the disease, condition or disorder; and (3) ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease.

Combination Therapies

One or more additional pharmaceutical agents such as, for example, chemotherapeutics, anti-inflammatory agents, steroids, immunosuppressants, as well as Bcr-Abl, Flt-3, RAF and FAK kinase inhibitors such as, for example, those described in WO 2006/056399, or other agents can be used in combination with the compounds of the present invention for treatment of JAK-associated diseases, disorders or conditions. The one or more additional pharmaceutical agents can be administered to a patient simultaneously or sequentially.

Example chemotherapeutics include proteosome inhibitors (e.g., bortezomib), thalidomide, revlimid, and DNA-damaging agents such as melphalan, doxorubicin, cyclophosphamide, vincristine, etoposide, carmustine, and the like.

Example steroids include coriticosteroids such as dexamethasone or prednisone.

Example Bcr-Abl inhibitors include the compounds, and pharmaceutically acceptable salts thereof, of the genera and species disclosed in U.S. Pat. No. 5,521,184, WO 04/005281, EP2005/009967, EP2005/010408, and U.S. Ser. No. 60/578,491.

Example suitable Flt-3 inhibitors include compounds, and their pharmaceutically acceptable salts, as disclosed in WO 03/037347, WO 03/099771, and WO 04/046120.

Example suitable RAF inhibitors include compounds, and their pharmaceutically acceptable salts, as disclosed in WO 00/09495 and WO 05/028444.

Example suitable FAK inhibitors include compounds, and their pharmaceutically acceptable salts, as disclosed in WO 04/080980, WO 04/056786, WO 03/024967, WO 01/064655, WO 00/053595, and WO 01/014402.

In some embodiments, one or more of the metabolites of the invention can be used in combination with one or more other kinase inhibitors including imatinib, particularly for treating patients resistant to imatinib or other kinase inhibitors.

In some embodiments, one or more JAK inhibitors of the invention can be used in combination with a chemotherapeutic in the treatment of cancer, such as multiple myeloma, and may improve the treatment response as compared to the response to the chemotherapeutic agent alone, without exacerbation of its toxic effects. Examples of additional pharmaceutical agents used in the treatment of multiple myeloma, for example, can include, without limitation, melphalan, melphalan plus prednisone [MP], doxorubicin, dexamethasone, and Velcade (bortezomib). Further additional agents used in the treatment of multiple myeloma include Bcr-Abl, Flt-3, RAF and FAK kinase inhibitors. Additive or synergistic effects are desirable outcomes of combining a JAK inhibitor of the present invention with an additional agent. Furthermore, resistance of multiple myeloma cells to agents such as dexamethasone may be reversible upon treatment with a JAK inhibitor of the present invention. The agents can be combined with the present compounds in a single or continuous dosage form, or the agents can be administered simultaneously or sequentially as separate dosage forms.

In some embodiments, a corticosteroid such as dexamethasone is administered to a patient in combination with at least one JAK inhibitor where the dexamethasone is administered intermittently as opposed to continuously.

In some further embodiments, combinations of one or more JAK inhibitors of the invention with other therapeutic agents can be administered to a patient prior to, during, and/or after a bone marrow transplant or stem cell transplant.

Pharmaceutical Formulations and Dosage Forms

When employed as pharmaceuticals, the compounds of the invention can be administered in the form of pharmaceutical compositions. These compositions can be prepared in a manner well known in the pharmaceutical art, and can be administered by a variety of routes, depending upon whether local or systemic treatment is desired and upon the area to be treated. Administration may be topical (including transdermal, epidermal, ophthalmic and to mucous membranes including intranasal, vaginal and rectal delivery), pulmonary (e.g. by inhalation or insufflation of powders or aerosols, including by nebulizer; intratracheal or intranasal), oral or parenteral. Parenteral administration includes intravenous, intraarterial, subcutaneous, intraperitoneal, intramuscular injection or infusion; or intracranial, e.g. intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

This invention also includes pharmaceutical compositions which contain, as the active ingredient, one or more of the compounds of the invention above in combination with one or more pharmaceutically acceptable carriers (excipients). In making the compositions of the invention, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh.

The compounds of the invention may be milled using known milling procedures such as wet milling to obtain a particle size appropriate for tablet formation and for other formulation types. Finely divided (nanoparticulate) preparations of the compounds of the invention can be prepared by processes known in the art, for example see International Patent Application No. WO 2002/000196.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The compositions can be formulated in a unit dosage form, each dosage containing from about 5 to about 1000 mg (1 g), more usually about 100 to about 500 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, about 0.1 to about 1000 mg of the active ingredient of the present invention.

The tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions can be nebulized by use of inert gases. Nebulized solutions may be breathed directly from the nebulizing device or the nebulizing device can be attached to a face masks tent, or intermittent positive pressure breathing machine. Solution, suspension, or powder compositions can be administered orally or nasally from devices which deliver the formulation in an appropriate manner.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of the compounds of the present invention can vary according to, for example, the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral administration. Some typical dose ranges are from about 1 μg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

The compositions of the invention can further include one or more additional pharmaceutical agents such as a chemotherapeutic, steroid, anti-inflammatory compound, or immunosuppressant, examples of which are listed hereinabove.

Labeled Compounds and Assay Methods

Another aspect of the present invention relates to labeled compounds of the invention (radio-labeled, fluorescent-labeled, etc.) that would be useful not only in imaging techniques but also in assays, both in vitro and in vivo, for localizing and quantitating JAK in tissue samples, including human, and for identifying JAK ligands by inhibition binding of a labeled compound. Accordingly, the present invention includes JAK assays that contain such labeled compounds.

The present invention further includes isotopically-labeled compounds of the invention. An "isotopically" or "radio-labeled" compound is a compound of the invention where one or more atoms are replaced or substituted by an atom having an atomic mass or mass number different from the atomic mass or mass number typically found in nature (i.e., naturally occurring). Suitable radionuclides that may be incorporated in compounds of the present invention include but are not limited to $^2$H (also written as D for deuterium), $^3$H (also written as T for tritium), $^{11}$C, $^{13}$C, $^{14}$C, $^{13}$N, $^{15}$N, $^{15}$O, $^{17}$O, $^{18}$O, $^{18}$F, $^{35}$S, $^{36}$Cl, $^{82}$Br, $^{75}$Br, $^{76}$Br, $^{77}$Br, $^{123}$I, $^{124}$I, $^{125}$I and $^{131}$I. The radionuclide that is incorporated in the instant radio-labeled compounds will depend on the specific application of that radio-labeled compound. For example, for in vitro metalloprotease labeling and competition assays, compounds that incorporate $^3$H, $^{14}$C, $^{82}$Br, $^{125}$I, $^{131}$I, $^{35}$S or will generally be most useful. For radio-imaging applications $^{11}$C, $^{18}$F, $^{125}$I, $^{123}$I, $^{124}$I, $^{131}$I, $^{75}$Br, $^{76}$Br or $^{77}$Br will generally be most useful.

It is understood that a "radio-labeled" or "labeled compound" is a compound that has incorporated at least one radionuclide. In some embodiments the radionuclide is selected from the group consisting of $^3$H, $^{14}$C, $^{125}$I, $^{35}$S and $^{82}$Br.

The present invention can further include synthetic methods for incorporating radio-isotopes into compounds of the invention. Synthetic methods for incorporating radio-isotopes into organic compounds are well known in the art, and a person of ordinary skill in the art will readily recognize the methods applicable for the compounds of invention.

A labeled compound of the invention can be used in a screening assay to identify/evaluate compounds. For example, a newly synthesized or identified compound (i.e., test compound) which is labeled can be evaluated for its ability to bind a JAK by monitoring its concentration variation when contacting with the JAK, through tracking of the labeling. For example, a test compound (labeled) can be evaluated for its ability to reduce binding of another compound which is known to bind to a JAK (i.e., standard compound). Accordingly, the ability of a test compound to compete with the standard compound for binding to the JAK directly correlates to its binding affinity. Conversely, in some other screening assays, the standard compound is labeled and test compounds are unlabeled. Accordingly, the concentration of the labeled standard compound is monitored in order to evaluate the competition between the standard compound and the test compound, and the relative binding affinity of the test compound is thus ascertained.

Kits

The present invention also includes pharmaceutical kits useful, for example, in the treatment or prevention of JAK-associated diseases or disorders, such as cancer, which include one or more containers containing a pharmaceutical composition comprising a therapeutically effective amount of a compound of the invention. Such kits can further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

The invention will be described in greater detail by way of specific examples. The following examples are offered for illustrative purposes, and are not intended to limit the invention in any manner. Those of skill in the art will readily recognize a variety of noncritical parameters which can be changed or modified to yield essentially the same results.

EXAMPLES

Example 1

3-[(1S,3R)-3-hydroxycyclopentyl]-3-[4-(7H-pyrrolo [2,3-d]pyrimidin-4-yl)-1H-pyrazol-1-yl]propanenitrile and 3-[(1R,3S)-3-hydroxycyclopentyl]-3-[4-(7H-pyrrolo[2,3-d]pyrimidin-4-yl)-1H-pyrazol-1-yl] propanenitrile

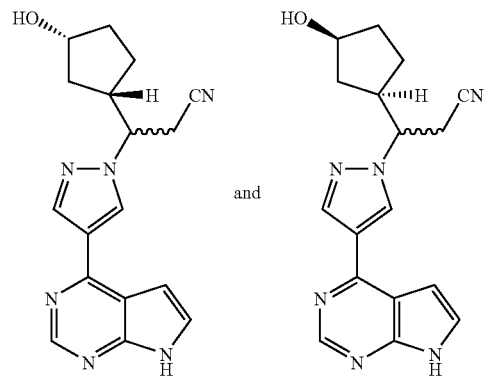

Step 1. 6-bromo-2-oxabicyclo[2.2.1]heptan-3-one

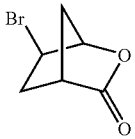

Bromotrimethysilane (3.1 mL, 0.023 mol) was added dropwise to a solution of dimethyl sulfoxide (1.6 mL, 0.023 mol) in chloroform (38.0 mL) in a round-bottom flask at 0° C. The resulting mixture was stirred at 0° C. for 2 hours. To the reaction mixture was added dropwise a solution of cyclopent-3-ene-1-carboxylic acid (2.00 g, 0.0178 mol) in chloroform (12 mL) over a period of 15 minutes and the reaction mixture was stirred at 0° C. for 10 minutes. N,N-diisopropylethylamine (4.0 mL, 0.023 mol) was then added and the resulting mixture was stirred at 0° C. After 10 minutes, the mixture was heated to reflux for 16 hours. The reaction mixture was diluted with chloroform, washed with water, brine, dried (MgSO$_4$), and stripped in vacuo. The residue was purified by chromatography on silica gel using 30% EtOAc/hexanes as eluent to give the product. $^1$H NMR (400 MHz, CDCl$_3$): δ 4.88 (brs, 1H), 4.34 (m, 1H), 2.90 (m, 1H), 2.66 (m, 1H), 2.31 (m, 1H), 1.93 (m, 1H), 1.83 (m, 1H).

Step 2. 2-oxabicyclo[2.2.1]heptan-3-one

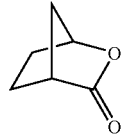

Tris(trimethylsilyl)silane (4.7 mL, 15 mmol) was added dropwise to a solution of 6-bromo-2-oxabicyclo[2.2.1]heptan-3-one (1.96 g, 10.3 mmol) and 2,2'-azo-bis-isobutyronitrile (0.2 g, 1 mmol) in toluene (100 mL) in a round-bottom flask and the resulting mixture was stirred at 80° C. for 5 hours. The reaction mixture was concentrated by rotoary evaporation and the residue was diluted with ethyl acetate, washed with saturated NH$_4$Cl, dried (MgSO$_4$), and stripped in vacuo. The residue was purified by chromatography on silica gel using 100% hexanes, grading to 25% EtOAc/hexanes then 33% EtOAc/hexanes as eluents to give the product. $^1$H NMR (300 MHz, CDCl$_3$): δ 4.93 (m, 1H), 2.91 (m, 1H), 2.19 (m, 1H), 1.60-1.99 (m, 5H).

Step 3. (2E)- and (2Z)-3-[(1S,3R)-3-hydroxycyclopentyl]acrylonitrile and (2E)- and (2Z)-[(1R,3S)-3-hydroxycyclopentyl]acrylonitrile

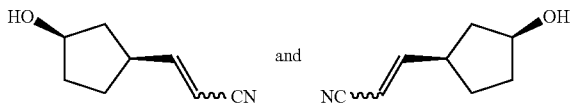

1.00 M of diisobutylaluminum hydride in toluene (8.0 mL) was added dropwise to a solution of 2-oxabicyclo[2.2.1]heptan-3-one (600 mg, 5 mmol) in methylene chloride (20 mL) in a round-bottom flask at −78° C. The resulting mixture was stirred at −78° C. for 45 minutes. The reaction mixture was treated with saturated Rochelle's salt solution. After stirring for 15 minutes, the reaction mixture was extracted with ethyl acetate and the combined organic extracts were washed with water, saturated NaCl, dried (MgSO$_4$), and stripped in vacuo. The crude product was used in the next reaction without further purification.

A solution of the crude 2-oxabicyclo[2.2.1]heptan-3-ol (400 mg, 4 mmol) and (triphenylphosphoranylidene)acetonitrile (1.2 g, 3.8 mmol) in toluene (12 mL) in a round-bottom flask was heated at 80° C. for 2 hours. The reaction mixture was then purified by chromatography on silica gel using 40% EtOAc/hexanes to give the racemic products. $^1$H NMR (400 MHz, CDCl$_3$): δ 6.78 (dd, 1H), 5.30 (d, 1H), 5.20 (m, 1H), 2.67 (m, 1H), 2.20 (m, 1H), 1.40-1.90 (m, 6H).

Step 4. 3-[(1S,3R)-3-hydroxycyclopentyl]-3-[4-(7-[2-(trimethylsilyl)ethoxy]methyl-7H-pyrrolo[2,3-d]pyrimidin-4-yl)-1H-pyrazol-1-yl]propanenitrile and 3-[(1R,3S)-3-hydroxycyclopentyl]-3-[4-(7-[2-(trimethylsilyl)ethoxy]methyl-7H-pyrrolo[2,3-d]pyrimidin-4-yl)-]H-pyrazol-1-yl]propanenitrile

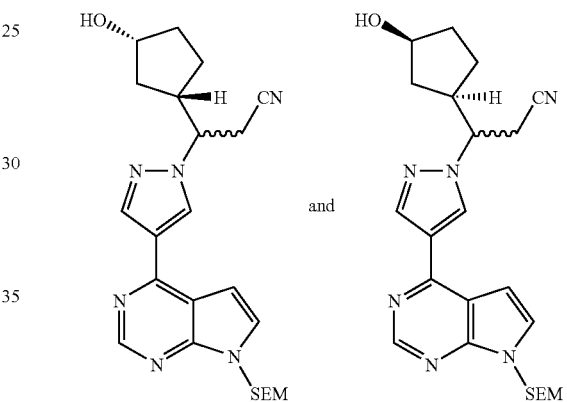

1,8-Diazabicyclo[5.4.0]undec-7-ene (0.54 mL, 3.6 mmol) was added to a solution of a mixture of (2E)- and (2Z)-3-[(1S,3R)-3-hydroxycyclopentyl]acrylonitrile and (2E)- and (2Z)-3-[(1R,3S)-3-hydroxycyclopentyl]acrylonitrile (0.250 g, 1.82 mmol) and 4-(1H-pyrazol-4-yl)-7-[2-(trimethylsilyl)ethoxy]methyl-7H-pyrrolo[2,3-d]pyrimidine (0.57 g, 1.8 mmol) in acetonitrile (5 mL) in a round-bottom flask. The resulting mixture was stirred at 25° C. for 2 days at which time LCMS analysis showed ~80% of the starting materials had been consumed. The reaction mixture was purified by chromatography on silica gel using 1:1 EtOAc/hexanes to give the product. $^1$H NMR (400 MHz, CDCl$_3$): δ 8.90 (d, 1H), 8.39 (m, 2H), 7.46 (m, 1H), 6.86 (m 1H), 5.73 (s, 2H), 4.52 (m, 2H), 3.59 (m, 2H), 3.2 (m, 1H), 3.02 (m, 1H), 2.78 (m, 1H), 2.3 (m, 1H), 1.30-1.90 (m, 6H), 0.99 (m, 2H), 0.08 (s, 9H). LC/MS: 453 (M+H)$^+$.

Step 5. 3-[(1S,3R)-3-hydroxycyclopentyl]-3-[4-(7H-pyrrolo[2,3-d]pyrimidin-4-yl)-1H-pyrazol-1-yl]propanenitrile and 3-[(1R,3S)-3-hydroxycyclopentyl]-3-[4-(7H-pyrrolo[2,3-d]pyrimidin-4-yl)-1H-pyrazol-1-yl]propanenitrile Lithium tetrafluoroborate (0.176 g, 1.88 mmol) was added to a solution of 3-[(1S,3R)-3-hydroxycyclopentyl]-3-[4-(7-[2-(trimethylsilyl)ethoxy]methyl-7H-pyrrolo[2,3-d]pyrimidin-4-yl)-1H-pyrazol-1-yl]propanenitrile and 3-[(1R,3S)-3-hydroxycyclopentyl]-3-[3-(7-[2-(trimethylsilyl)ethoxy]

methyl-7H-pyrrolo[2,3-d]pyrimidin-4-yl)-1H-pyrazol-1-yl]propanenitrile (85.0 mg, 0.188 mmol) in acetonitrile (1.5 mL) and water (0.135 mL) in a vial. The resulting mixture was heated at 85° C. for 26 hours. After the reaction mixture was allowed to cool to 25° C., ethylenediamine (63 µL, 0.94 mmol) was added and the resulting mixture was stirred at 25° C. for 3 hours. The reaction mixture was purified by prep. LC to give the product as the trifluoroaceticacid salt. This was dissolved in methanol and Amberlyst 26 was added. The resulting mixture was stirred for 10 minutes, filtered, and concentrated. The residue was purified by chiral chromatography to give 4 major peaks and 4 minor peaks. (Column: ChiralPak IA, 4.6×250 mm, 5 micron particle. Mobile phase: 30% Ethanol in hexanes. Flow Rate: 0.8 ml/min-analytical; Column: ChiralPak IA, 20×250 mm, 5 micron particle. Mobile Phase: 30% Ethanol in hexanes. Flow rate: 12 ml/min-preparative)

The minor peaks were attributed to the trifluoroacetate esters which are very mobile and are cleaved on standing in methanol to the corresponding alcohols.

Major Peak 1 [Retention time: 18.56 minutes]: $^1$H NMR (400 MHz, CD$_3$OD): δ 8.66 (brs, 1H), 8.64 (s, 1H), 8.38 (s, 1H), 7.51 (m, 1H), 6.97 (m, 1H), 4.57 (m, 1H), 4.20 (m, 1H), 3.16 (m, 2H), 2.65 (m, 1H), 1.64-2.00 (m, 5H), 1.28 (m, 1H). LC/MS: 323 (M+H)$^+$.

Major Peak 2 [Retention time: 25.88 minutes]: $^1$H NMR (400 MHz, CD$_3$OD): δ 8.66 (brs, 1H), 8.64 (s, 1H), 8.38 (s, 1H), 7.50 (m, 1H), 6.96 (m, 1H), 4.60 (m, 1H), 4.30 (m, 1H), 3.18 (m, 2H), 2.61 (m, 1H), 2.23 (m, 1H), 1.40-1.80 (m, 5H). LC/MS: 323 (M+H)$^+$.

Major Peak 3 [Retention time: 39.84 minutes]: $^1$H NMR (400 MHz, CD$_3$OD): δ 8.66 (brs, 1H), 8.64 (s, 1H), 8.38 (s, 1H), 7.50 (m, 1H), 6.96 (m, 1H), 4.60 (m, 1H), 4.30 (m, 1H), 3.18 (m, 2H), 2.61 (m, 1H), 2.23 (m, 1H), 1.40-1.80 (m, 5H). LC/MS: 323 (M+H)$^+$.

Major Peak 4 [Retention time: 51.48 minutes]: $^1$H NMR (400 MHz, CD$_3$OD): δ 8.66 (brs, 1H), 8.64 (s, 1H), 8.38 (s, 1H), 7.51 (m, 1H), 6.97 (m, 1H), 4.57 (m, 1H), 4.20 (m, 1H), 3.16 (m, 2H), 2.65 (m, 1H), 1.64-2.00 (m, 5H), 1.28 (m, 1H). LC/MS: 323 (M+H)$^+$.

Example 2

3-[(1S,3S)-3-hydroxycyclopentyl]-3-[4-(7H-pyrrolo[2,3-d]pyrimidin-4-yl)-1H-pyrazol-1-yl]propanenitrile trifluoroacetic acid salt and 3-[(1R,3R)-3-hydroxycyclopentyl]-3-[4-(7H-pyrrolo[2,3-d]pyrimidin-4-yl)-1H-pyrazol-1-yl]propanenitrile trifluoroacetic acid salt

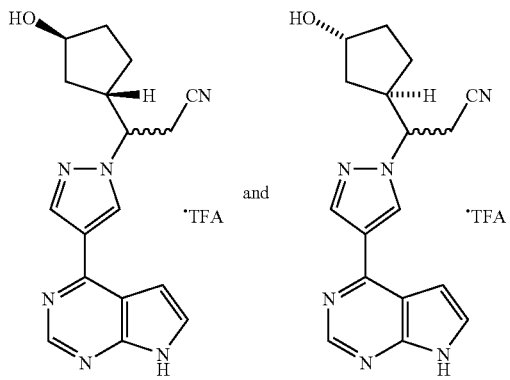

Step 1: (1S,3S)-3-{2-cyano-1-[4-(7-[2-(trimethylsilyl)ethoxy]methyl-7H-pyrrolo[2,3-d]pyrimidin-4-yl)-1H-pyrazol-1-yl]ethyl}cyclopentyl benzoate and (1R,3R)-3-{2-cyano-1-[4-(7-[2-(trimethylsilyl)ethoxy]methyl-7H-pyrrolo[2,3-d]pyrimidin-4-yl)-1H-pyrazol-1-yl]ethyl}cyclopentyl benzoate Diisopropyl azodicarboxylate (0.38 mL, 1.9 mmol) was added to a solution of 3-[(1S,3R)-3-hydroxycyclopentyl]-3-[4-(7-[2-(trimethylsilyl)ethoxy]methyl-7H-pyrrolo[2,3-d]pyrimidin-4-yl)-1H-pyrazol-1-yl]propanenitrile and 3-[(1R,3S)-3-hydroxycyclopentyl]-3-[4-(7-[2-(trimethylsilyl)ethoxy]methyl-7H-pyrrolo[2,3-d]pyrimidin-4-yl)-1H-pyrazol-1-yl]propanenitrile (0.51 g, 1.9 mmol) in tetrahydrofuran (5.3 mL) in a round-bottom flask at 0° C. The resulting mixture was stirred for 10 minutes and benzoic acid (0.24 g, 1.9 mmol) was added. The reaction mixture was stirred at 0° C. for 2 hours at which time TLC analysis showed no starting material. The reaction mixture was diluted with ethyl acetate, washed with sat. NaHCO$_3$, water, saturated NaCl, dried (MgSO$_4$), and stripped in vacuo. The residue was chromatographed on silica gel using 20% EtOAc/hexanes to give the product. $^1$H NMR (300 MHz, CDCl$_3$): δ 8.91 (d, 1H), 8.39 (m, 2H), 8.08 (m, 2H), 7.75 (m, 1H), 7.61 (m, 1H), 7.48 (m, 2H), 7.46 (m, 1H), 6.87 (m 1H), 5.74 (s, 2H), 5.40-5.50 (m, 1H), 4.40 (m, 1H), 3.60 (m, 2H), 3.25 (m, 1H), 3.07 (m, 1H), 2.27 (m, 2H), 1.30-1.90 (m, 6H), 0.99 (m, 2H), 0.08 (s, 9H). LC/MS: 557 (M+H)$^+$.

Step 2: 3-[(1S,3S)-3-hydroxycyclopentyl]-3-[4-(7-[2-(trimethylsilyl)ethoxy]methyl-7H-pyrrolo[2,3-d]pyrimidin-4-yl)-1H-pyrazol-1-yl]propanenitrile and 3-[(1R,3R)-3-hydroxycyclopentyl]-3-[4-(7-[2-(trimethylsilyl)ethoxy]methyl-7H-pyrrolo[2,3-d]pyrimidin-4-yl)-1H-pyrazol-1-yl]propanenitrile Lithium hydroxide (22.7 mg, 0.000948 mol) was added to a solution of (1S,3S)-3-{2-cyano-1-[4-(7-[2-(trimethylsilyl)ethoxy]methyl-7H-pyrrolo[2,3-d]pyrimidin-4-yl)-1H-pyrazol-1-yl]ethyl}cyclopentyl benzoate and (1R,3R)-3-{2-cyano-1-[4-(7-[2-(trimethylsilyl)ethoxy]methyl-7H-pyrrolo[2,3-d]pyrimidin-4-yl)-1H-pyrazol-1-yl]ethyl}cyclopentyl benzoate (440 mg, 0.00079 mol) dissolved in a mixture of 1,4-dioxane (10.0 mL, 0.128 mol), methanol (4.0 mL, 0.099 mol), and water (4.0 mL, 0.22 mol) in a round-bottom flask. The resulting mixture was stirred for 20 hours at which time LCMS analysis showed no starting material. The reaction mixture was extracted with ethyl acetate and the organic extracts were washed with sat. NaHCO$_3$, water, saturated NaCl, dried (MgSO$_4$), and stripped in vacuo. The residue was used in the next reaction without further purification. LC/MS: 453 (M+H)$^+$.

Step 3: 3-[(1S,3S)-3-hydroxycyclopentyl]-3-[4-(7H-pyrrolo[2,3-d]pyrimidin-4-yl)-1H-pyrazol-1-yl]propanenitrile trifluoroacetic acid salt and 3-[(1R,3R)-3-hydroxycyclopentyl]-3-[4-(7H-pyrrolo[2,3-d]pyrimidin-4-yl)-1H-pyrazol-1-yl]propanenitrile trifluoroacetic acid salt The mixture of 3-[(1S,3S)-3-hydroxycyclopentyl]-3-[4-(7-[2-(trimethylsilyl)ethoxy]methyl-7H-pyrrolo[2,3-d]pyrimidin-4-yl)-1H-pyrazol-1-yl]propanenitrile and 3-[(1R,3R)-3-hydroxycyclopentyl]-3-[4-(7-[2-(trimethylsilyl)ethoxy]methyl-7H-pyrrolo[2,3-d]pyrimidin-4-yl)-1H-pyrazol-1-yl]propanenitrile was deprotected under the same conditions described in Example 1, Step 5. The mixture was separated using chiral LC and further purified by LC to give the isomers as the trifluoroacetate salts. Column: ChiralPak IA, 4.6×250 mm, 5 micron particle. Mobile phase: 30% Ethanol in hexanes. Flow Rate: 0.8 ml/min-analytical; Column: ChiralPak IA, 20×250 mm, 5 micron particle. MobilePhase: 30% Ethanol in hexanes. Flow rate: 12 mmin preparative).

Pk1[Retention time: 16.98 minutes]: $^1$H (500 MHz, DMSO-$d_6$): δ 8.11 (brs, 1H), 8.07 (brs, 1H), 7.70 (s, 1H), 7.03 (d, 1H), 6.46 (m, 1H), 3.80 (m, 1H), 3.43 (m, 1H), 2.20 (m, 2H), 2.08 (m, 1H), 1.29 (m, 1H), 1.20 (m, 1H), 0.60-0.90 (m, 4H). LC/MS: 323 (M+H)$^+$.

Pk2[Retention time: 18.68 minutes]: $^1$H (500 MHz, CD$_3$OD): δ 8.91 (s, 1H), 8.087 (s, 1H), 8.51 (s, 1H), 7.84 (d, 1H), 7.28 (m, 1H), 4.60 (m, 1H), 4.34 (m, 1H), 3.20 (m, 2H), 2.91 (m, 1H), 1.92 (m, 2H), 1.60 (m, 3H), 1.35 (m, 1H). LC/MS: 323 (M+H)$^+$.

Pk3 and Pk4 eluted together (23.13 minutes).

Example 3

3-[(1S)-3-oxocyclopentyl]-3-[4-(7H-pyrrolo[2,3-d]pyrimidin-4-yl)-1H-pyrazol-1-yl]propanenitrile trifluoroacetate salt and 3-[(1R)-3-oxocyclopentyl]-3-[4-(7H-pyrrolo[2,3-d]pyrimidin-4-yl)-1H-pyrazol-1-yl]propanenitrile trifluoroacetic acid salt

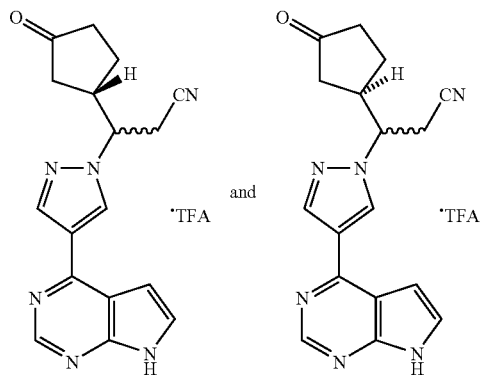

Step 1: 3-[(1S)-3-oxocyclopentyl]-3-[4-(7-[2-(trimethylsilyl)ethoxy]methyl-7H-pyrrolo[2,3-d]pyrimidin-4-yl)-1H-pyrazol-1-yl]propanenitrile and 3-[(1R)-3-oxocyclopentyl-3-[4-(7-[2-(trimethylsilyl)ethoxy]methyl-7H-pyrrolo[2,3-d]pyrimidin-4-yl)-1H-pyrazol-1-yl]propanenitrile Dimethyl sulfoxide (0.340 mL, 4.79 mmol) was added to a solution of oxalyl chloride (0.20 mL, 2.4 mmol) in methylene chloride (25 mL) −78° C. in a round-bottom flask. The resulting mixture was stirred at −78° C. for 15 minutes and a solution of 3-[(1S,3R)-3-hydroxycyclopentyl]-3-[4-(7-[2-(trimethylsilyl)ethoxy]methyl-7H-pyrrolo[2,3-d]pyrimidin-4-yl)-1H-pyrazol-1-yl]propanenitrile and 3-[(1R,3S)-3-hydroxycyclopentyl]-3-[4(7-[2-(trimethylsilyl)ethoxy]methyl-7H-pyrrolo[2,3-d]pyrimidin-4-yl)-1H-pyrazol-1-yl]propanenitrile (0.84 g, 1.8 mmol) in methylene chloride (17 mL) was added dropwise. The resulting mixture was stirred at −78° C. for 60 minutes and triethylamine (0.722 mL, 5.18 mmol) was added. After stirring at −78° C. for 60 minutes, the reaction mixture was warmed to 0° C. and stirred for 1 hour. The reaction mixture was diluted with ethyl acetate, washed with water, saturated NaCl, dried (MgSO$_4$), and stripped in vacuo. The residue was purified by chromatography on silica gel using 40% EtOAc/hexanes to give the product. $^1$H NMR (300 MHz, CDCl$_3$): δ 8.91 (m, 1H), 8.40 (d, 1H), 8.38 (s, 1H), 7.47 (m, 1H), 6.85 (t, 1H), 5.74 (s, 2H), 4.51 (m, 1H), 3.60 (t, 2H), 3.00-3.30 (m, 3H), 1.50-2.70 (m, 6H), 0.98 (t, 2H), 0.00 (s, 9H). LC/MS: 451 (M+H)$^+$.

Step 2: 3-[(1S)-3-oxocyclopentyl]-3-[4-(7H-pyrrolo[2,3-d]pyrimidin-4-yl)-1H-pyrazol-1-yl]propanenitrile trifluoroacetate salt and 3-[(1R)-3-oxocyclopentyl]-3-[4-(7H-pyrrolo[2,3-d]pyrimidin-4-yl)-1H-pyrazol-1-yl]propanenitrile trifluoroacetic acid salt The mixture of 3-[(1S)-3-oxocyclopentyl]-3-[4-(7-[2-(trimethylsilyl)ethoxy]methyl-7H-pyrrolo[2,3-d]pyrimidin-4-yl)-1H-pyrazol-1-yl]propanenitrile and 3-[(1R)-3-oxocyclopentyl]-3-[4-(7-[2-(trimethylsilyl)ethoxy]methyl-7H-pyrrolo[2,3-d]pyrimidin-4-yl)-1H-pyrazol-1-yl]propanenitrile was deprotected under conditions similar to Example 1, Step 5, to give the two diastereomeric ketones which were separated by chiral chromatography and purified by LC to give the diastereomers and enantiomers as the trifluoroacetate salts. Column: ChiralPak IA, 4.6×250 mm, 5 micron particle. Mobile phase: 30% Ethanol in hexanes. Flow Rate: 0.8 ml/min-analytical; Column: ChiralPak IA, 20×250 mm, 5 micron particle. MobilePhase: 30% Ethanol in hexanes. Flow rate: 12 ml/min preparative).

Pk1[Retention time: 11.82 minutes].

Pk2[Retention time: 13.94 minutes]: $^1$H (500 MHz, CDCl$_3$): δ 10.07 (brs, 1H), 8.79 (brs, 1H), 8.27 (s, 1H), 8.25 (s, 1H), 7.32 (d, 1H), 6.71 (m, 1H), 4.40 (m, 1H), 3.12 (m, 1H), 2.97 (m, 2H), 2.00-2.32 (m, 5H), 1.61 (m, 1H). LC/MS: 321 (M+H)$^+$.

Pk3 [Retention time: 17.61 minutes]: $^1$H (500 MHz, CDCl$_3$): δ 10.70 (brs, 1H), 8.83 (brs, 1H), 8.34 (s, 1H), 8.30 (s, 1H), 7.35 (d, 1H), 6.73 (m, 1H), 4.37 (m, 1), 3.10 (m, 1H), 2.90 (m, 2H), 2.51 (m, 1H), 2.27 (m, 1H), 2.15 (m, 1H), 1.91 (m, 1H), 1.84 (m, 1H), 1.60 (m, 1H). LC/MS: 321 (M+H)$^+$.

Pk4 [Retention time: 20.31 minutes].

Example A

TABLE 2

| Compound | JAK 1 IC50 (nM) | JAK 2 IC50 (nM) | JAK 3 IC50 (nM) | Fraction Unbound (% human serum) | Human Intrinsic CL (L/h/kg) |
|---|---|---|---|---|---|
| Compound 1 | <10 | <10 | <10 | <5 | 0.68 |
| Metabolite 1 | 2.5-12 | 0.7-2.5 | 8.3-45 | 26-35 | <0.50 |
| Metabolite 2 | 3-15 | 2-2.8 | 17-30 | 5-27 | <0.50 |
| Metabolite 3 | 2.7-12 | 2.1-5.9 | 11-41 | 14-56 | <0.57 |

Metabolites 1, 2, and 3 were isolated from rat or dog urine after administration of Compound 1 in connection with pharmacokinetic and toxicokinetic studies. Activity data for Metabolites 1, 2, and 3, along with free fraction and intrinsic clearance data, was compared with that for the parent compound, Compound 1. JAK activity assays, free fraction assays, and intrinsic clearance assays are described below. Data points were obtained for some individual stereoisomers of Metabolites 1, 2, and 3, and the numerical range provided above reflects the highest and lowest values obtained for all the stereoisomers tested. As can be seen in Table 1, the metabolites are potent inhibitors of JAK1, JAK2, and JAK3, like Compound 1. However, the free fractions obtained for the metabolites are unexpectedly higher and the intrinsic clearance desirably lower than for Compound 1.

In Vitro JAK Kinase Assay

Compounds herein were tested for inhibitory activity of JAK targets according to the following in vitro assay described in Park et al., *Analytical Biochemistry* 1999, 269, 94-104. The catalytic domains of human JAK1 (a.a. 837-1142), Jak2 (a.a. 828-1132) and Jak3 (a.a. 781-1124) with an N-terminal His tag were expressed using baculovirus in insect cells and purified. The catalytic activity of JAK1, JAK2 or JAK3 was assayed by measuring the phosphorylation of a biotinylated peptide. The phosphorylated peptide was detected by homogenous time resolved fluorescence (HTRF). $IC_{50}$s of compounds were measured for each kinase in the reactions that contain the enzyme, ATP and 500 nM peptide in 50 mM Tris (pH 7.8) buffer with 100 mM NaCl, 5 mM DTT, and 0.1 mg/mL (0.01%) BSA. The ATP concentration in the reactions was 90 µM for Jak1, 30 µM for Jak2 and 3 µM for Jak3. Reactions were carried out at room temperature for 1 hr and then stopped with 20 µL 45 mM EDTA, 300 nM SA-APC, 6 nM Eu-Py20 in assay buffer (Perkin Elmer, Boston, Mass.). Binding to the Europium labeled antibody took place for 40 minutes and HTRF signal was measured on a Fusion plate reader (Perkin Elmer, Boston, Mass.). Compounds having an $IC_{50}$ of 10 µM or less for any of the above-mentioned JAK targets were considered active.

Free Fraction Assay

The protein binding of a test compound was determined by equilibrium dialysis using a Dianorm system from Harvard Apparatus (Holliston, Mass.). The dialysis was performed at 37° C. for 2 hrs in human serum. The metabolites were incubated at 3 µM, and Compound 1 at 3 and 10 µM. The compound concentrations in serum and buffer post-dialysis were determined by LC/MS/MS analysis. Free fraction is defined as the ratio of the buffer versus serum concentration.

Intrinsic Clearance Assay

Intrinsic clearance was determined by incubating 1 µM of test compound in human mixed gender liver microsomes (0.5 mg/mL protein) at 37° C. in the presence of 1 mM NADPH. The disappearance of the test compound was monitored by LC/MS at 0, 5, 10, 20 and 30 min. The slope of decline in compound concentration was used to calculate the human intrinsic clearance by employing standard methods reported in the literature.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

What is claimed is:

1. A compound selected from:
   3-(4-(7H-pyrrolo[2,3-d]pyrimidin-4-yl)-1H-pyrazol-1-yl)-3-(3-hydroxycyclopentyl) propanenitrile;
   3-(4-(7H-pyrrolo[2,3-d]pyrimidin-4-yl)-1H-pyrazol-1-yl)-3-(2-hydroxycyclopentyl) propanenitrile; and
   3-(4-(7H-pyrrolo[2,3-d]pyrimidin-4-yl)-1H-pyrazol-l-yl)-3-(3-oxocyclopentyl) propanenitrile,
   or a pharmaceutically acceptable salt thereof;
   which is substantially isolated.

2. A composition comprising a compound of claim 1, or a pharmaceutically acceptable salt thereof, and at least one pharmaceutically acceptable carrier.

3. The composition of claim 2 which is suitable for oral administration.

4. A method of treating a disease in a patient, wherein said disease is associated with Janus kinase activity, comprising administering to said patient a therapeutically effective amount of a compound of claim 1, or a pharmaceutically acceptable salt thereof, wherein said disease is allograft rejection or graft versus host disease.

5. A composition according to claim 2, containing at least about 50% by weight of said compound or said salt.

6. A composition according to claim 2, containing at least about 90% by weight of said compound or said salt.

7. A composition according to claim 2, containing at least about 95% by weight of said compound or said salt.

8. A composition according to claim 2, containing at least about 99% by weight of said compound or said salt.

9. A compound according to claim 1, which is 3-(4-(7H-pyrrolo[2,3-d]pyrimidin-4-yl)-1H-pyrazol-1-yl)-3-(3-hydroxycyclopentyl)propanenitrile, or a pharmaceutically acceptable salt thereof.

10. A compound according to claim 1, which is 3-(4-(7H-pyrrolo[2,3-d]pyrimidin-4-yl)-1H-pyrazol-1-yl)-3-(2-hydroxycyclopentyl)propanenitrile, or a pharmaceutically acceptable salt thereof.

11. A compound according to claim 1, which is 3-(4-(7H-pyrrolo[2,3-d]pyrimidin-4-yl)-1H-pyrazol-1-yl)-3-(3-oxo-cyclopentyl)propanenitrile, or a pharmaceutically acceptable salt thereof.

* * * * *